United States Patent [19]

Simjian

[11] Patent Number: 4,776,331
[45] Date of Patent: Oct. 11, 1988

[54] BANDAGE

[75] Inventor: Luther G. Simjian, Fort Lauderdale, Fla.

[73] Assignee: Command Automation, Inc., Fort Lauderdale, Fla.

[21] Appl. No.: 878,173

[22] Filed: Jun. 25, 1986

Related U.S. Application Data

[63] Continuation-in-part of Ser. No. 837,562, Mar. 7, 1986, abandoned.

[51] Int. Cl.$^4$ .............................................. A61F 13/00
[52] U.S. Cl. ..................................... 128/169; 128/155; 128/783; 116/270
[58] Field of Search ............... 128/156, 327, 782, 155, 128/165, 169, 798; 604/306; 116/270

[56] References Cited

U.S. PATENT DOCUMENTS

| | | | |
|---|---|---|---|
| 3,306,292 | 2/1967 | Spees | 604/306 |
| 3,613,679 | 10/1971 | Bijou | 128/169 |
| 4,133,307 | 1/1979 | Ness | 128/75 |
| 4,213,463 | 7/1980 | Osenkarski | 128/798 X |
| 4,421,124 | 12/1983 | Marshall | 128/782 |
| 4,502,491 | 3/1985 | Ender et al. | 128/782 |

Primary Examiner—Richard J. Apley
Assistant Examiner—John Welsh

[57] ABSTRACT

A bandage useful, for instance, in medical applications includes a rupturable sheet or strip having encapsulated fluid (liquid or gas). The sheet or strip is disposed between the body portion to be bandaged and the outer surface of the bandage. The sheet or strip ruptures when a predetermined pressure is exceeded, thereby releasing the fluid for indicating that the bandage is applied too tightly. When the fluid is a liquid, such as a dye, the released liquid will stain the bandage. When the fluid is a gaseous substance, the release of the gas will be sensed. When a plurality of strips are used, one strip may contain a liquid and another one a gaseous substance, the strips rupturing at different predetermined pressures.

8 Claims, 1 Drawing Sheet

BANDAGE

This application is a continuation in-part application of my copending application for U.S. Letters Patent, Ser. No. 06/837,582 filed Mar. 7, 1986, which application will be abandoned by being superseded by this application.

BACKGROUND OF THE INVENTION

This invention broadly relates to a bandage and, more specifically, refers to a bandage which includes a pressure sensitive fluid filled medium adapted to rupture responsive to predetermined pressure for causing the fluid (liquid or gas) to be released for providing a visual, odoriferous or other indication that the bandage is too tightly applied.

Most surgical procedures require the use of a medical bandage over the affected area in order to protect the wound, incision, exposed body tissue, etc. and to promote healing. Generally, a bandage of cotton, gauze or other suitable medium is used. A moisture resistant material may form the outer cover layer. When an orthopedic procedure is involved, frequently a plaster cast is required to immobilize a limb. It is common practice to use a thin layer of gauze over which the plaster cast is applied.

Plaster casts and bandages which are applied too tightly over the skin or wound, not only present problems in promoting sound healing, but also are uncomfortable to the patient. Particularly in the field of cosmetic facial surgery, it has been reported that bandages which are too tightly applied cause undesirable side effects, such as severe ear aches. It is then necessary to promptly remove such a bandage and re-apply it upon the patient.

The present invention addresses itself to this problem and provides for the use of a rupturable medium containing encapsulated fluid. The medium, preferably, is in sheet or strip form and is disposed between the affected body area and the overlying bandage or disposed between the affected body area and the overlying bandage or cast. If the bandage or cast is too tight while applied to the affected area, the medium ruptures and the fluid (liquid or gas) now released, will penetrate into the bandage or cast to thereby provide a visual or odoriferous indication of a bandage deemed too tight. When the fluid is a liquid, such as a dye, the released liquid will stain the bandage to provide a visual indication. When the fluid is an odorous gas, the released gas will penetrate through the bandage and provide an indication to olfactory organs.

As a part of this invention, it will be possible to use a plurality of strips of encapsulated fluid, each strip rupturable at a slightly different pressure and each containing a different fluid, such as different color dyes. Therefore, the physician will obtain a more detailed indication of the prevailing pressure condition.

One of the important objects of this invention is the provision a new and improved bandage.

Another important object of this invention is the provision of a new and improved method for providing bandages having pressure responsive indicating means.

Another important object of this invention is the provision of a medical bandage and method for bandaging which include means for indicating the condition when the pressure applied by the bandage is too great.

A further important object of this invention is the provision of a medical bandage which includes a rupturable medium in strip or sheet form containing an encapsulated fluid in liquid or gaseous form, such fluid being released responsive to a predetermined pressure applied thereupon.

Still further and other important objects of this invention will become more clearly apparent from the following description when taken in conjunction with the accompanying drawings.

DETAILED DESCRIPTION OF THE INVENTION

The use of encapsulated dye material in a medium and subject to rupture responsive to pressure for providing a visual indication is well known. A typical product of this type is the carbon-less paper in which the reverse side of the paper is provided with micro-encapsulated dye. When writing on such paper, the medium is ruptured and dye material is released and transferred upon an underlying sheet of paper. In this manner, the use of carbon paper is eliminated.

In another application, an odoriferous gaseous substance is encapsulated on a sheet of paper, the gas being released responsive to scratching the sheet for teaching persons to recognize the smell of escaping cooking gas. In another application, air is encapsulated in plastic sheeting to provide a cushioning material used for packaging delicate articles. While the plastic material used for encapsulating air generally is of such thickness as to be burst resistant, nevertheless given sufficient pressure, it can be ruptured to thereby release the encapsulated volume of air.

As will be noted from the above prior art description, the encapsulating of a liquid dye and of gas in a rupturable medium is well known.

Figure 1:
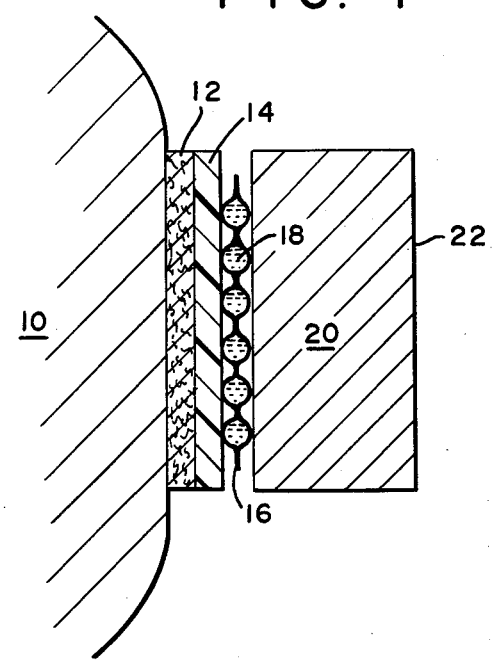
FIG. 1 is a sectional view of the bandage in accordance with the invention.

Referring now to the figures and FIG. 1 in particular, there is shown a portion 10 of a human body upon which the bandage comprising this invention is applied. The bandage, in a typical embodiment, comprises a thin layer of gauze 12 superposed on the body portion 10, a liquid barrier layer 14, such as a thin layer of plastic film, a rupturable medium 16 containing places of encapsulated liquid dye 18 and a final bandage material 20 having an exposed outer surface 22. The term bandage 20, as used in this specification may be a soft bandage which is applied on the portion 10 or may comprise a plaster cast as used primarily in orthopedic procedures.

The medium 16 in a typical example may comprise thin flexible plastic film, or gelatin material or other suitable substance adapted to contain a dye 18 in an encapsulated manner. The dye 18 preferably is a vegetable base dye, but can be a dye made from other substances. It may be encapsulated in liquid or semi-liquid form, but is designed to flow freely when released.

In the event that the bandage 20 is applied too tightly upon the body portion 10, the medium 16 will rupture at one or more places, thereby releasing encapsulated dye 18. The dye, generally of a contrasting color, will penetrate into the bandage layer 20, causing it to be stained and thereby providing a visual indication in the form of a stain at the exposed surface 22. The barrier layer 14 prevents the dye from running upon the body portion 10 which may contain an open wound. If this is of no concern, the barrier layer 14 can be omitted.

Figure 2:
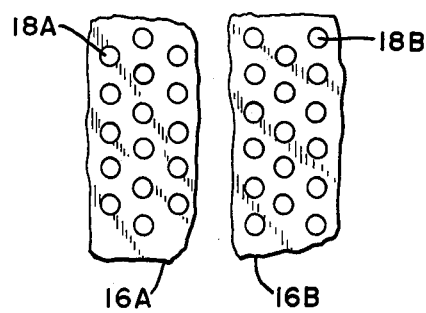
FIG. 2 is a plan view of the rupturable medium containing encapsulated dye.

The medium 16 may be in sheet form or alternatively may be in strip form as shown in FIG. 2. For instance, as shown in this figure, two strips 16A and 16B may be used in side-by-side relation. Strip 16A contains encapsulated dye 18A of a first color and strip 16B contains dye 18B of a second color. If the medium of strip 16A ruptures responsive to a lower pressure than that of medium of strip 16B, the physician will receive an indication of the severity of the problem, or whether the pressure is just right if the strip 16A is made to rupture responsive to normal pressure conditions. It will be apparent that some experimentation will be required as different portions of the human body can accept different predermined levels of pressure.

If the bandage is readily stained responsive to the flow of liquid and such staining is readily discernible upon visual inspection, the encapsulated liquid can be colorless.

In an alternative embodiment of the present invention the encapsulated fluid comprises an odoriferous gaseous substance. The release of the odoriferous gas can be discerned by the attending physician. As described above, the strips 16A and 16B may contain gaseous substances with different odors, such as sweet and sour smelling substances, for discerning which of the strips has been ruptured. In a still further alternative embodiment, one strip may contain a liquid while the other strip, rupturable at a different pressure, may contain an odoriferous gas.

As shown in FIGS. 1 and 2, the medium 16 in sheet or strip form may comprise a part of a partially assembled bandage or alternatively, the strips 16A, 16B may be furnished separately, and inserted into the bandage assembly during bandaging of the body portion.

In a further alternative embodiment, the medium includes encapsulated gas, the rupturing of the medium and the resultant release of the gas being sensed during bandaging by suitable sensing means, such as a microphone or stethoscope, if the audible noise is audible at too low a level for being audible without instrumentation.

While it is believed that the above described invention is primarily suited for medical purposes, it should be understood that the invention may also be useful in other applications where a delicate article needs to be protected during use, shipping or other critical situations.

While there have been described and illustrated several preferred embodiments of my invention, it will be apparent to those skilled in the art, that various further changes and modifications may be made without deviating from the broad principle of my invention which shall be limited only by the scope of the appended claims.

I claim:

1. The method of providing a bandage including the steps of disposing between the body portion to be bandaged and the outer surface of the bandage a plurality of flexible strips, each strip comprising a pressure responsive rupturable medium containing fluid in an encapsulated form, and each of said media being rupturable at a different pressure and containing a different fluid, whereby responsive to pressure of the bandage upon said medium encapsulated fluid of a respective strip is released.

2. The method of providing a bandage as set forth in claim 1, said fluid comprising dyes of different color.

3. The method of providing a bandage as set forth in claim 1, said fluid comprising gaseous substances having different odors.

4. The method of providing a bandage as set forth in claim 1, one of said strips containing a dye and one other of said strips containing an odoriferous gaseous substance.

5. A bandage including as a part thereof a plurality of flexible strips disposed between a body portion to be protected by said bandage and the outer surface of said bandage, each strip comprising a pressure responsive rupturable medium containing fluid in an encapsulated form, and each of said media being rupturable at a different pressure and containing a different fluid, whereby responsive to pressure of the bandage upon said medium encapsulated fluid of a respective strip is released.

6. A bandage as set forth in claim 5, said fluid comprising dyes of different color.

7. A bandage as set forth in claim 5, said fluid comprising gaseous substances having different odors.

8. A bandage as set forth in claim 5, one of said strips containing a dye and one other one of said strips containing an odoriferous gaseous substance

* * * * *